US007789843B2

(12) United States Patent
Ray

(10) Patent No.: US 7,789,843 B2
(45) Date of Patent: Sep. 7, 2010

(54) HEAD POSITIONING DEVICE FOR TREATMENT OF SLEEP APNEA

(75) Inventor: Charles D. Ray, Santa Barbara, CA (US)

(73) Assignee: Novara, LC, Santa Barbara, CA (US)

( * ) Notice: Subject to any disclaimer, the term of this patent is extended or adjusted under 35 U.S.C. 154(b) by 267 days.

(21) Appl. No.: 11/618,994

(22) Filed: Jan. 2, 2007

(65) Prior Publication Data
US 2008/0156332 A1    Jul. 3, 2008

(51) Int. Cl.
*A61F 5/56* (2006.01)
(52) U.S. Cl. .............................. 602/18; 602/17; 602/32; 602/902; 128/845; 128/846; 128/848; 27/25.1
(58) Field of Classification Search ...................... 602/5, 602/12, 16, 18, 19, 32, 902, 17; 128/848, 128/DIG. 23, 845, 846; 27/25.1; 2/468; 5/617, 622, 637, 640; 351/245; 606/240
See application file for complete search history.

(56) References Cited

U.S. PATENT DOCUMENTS

| 197,243 | A | * | 11/1877 | Boylston | 27/25.1 |
| 402,764 | A | * | 5/1889 | Nunn | 27/25.1 |
| 771,982 | A | * | 10/1904 | Hiser | 27/25.1 |
| 3,776,224 | A | * | 12/1973 | McFarland | 602/18 |
| 5,289,829 | A | * | 3/1994 | Roehrig | 128/848 |
| 6,171,314 | B1 | * | 1/2001 | Rotramel | 606/106 |
| 6,315,746 | B1 | * | 11/2001 | Garth et al. | 602/18 |
| 6,423,020 | B1 | * | 7/2002 | Koledin | 602/18 |
| 2003/0167018 | A1 | | 9/2003 | Wyckoff | |
| 2004/0204666 | A1 | * | 10/2004 | Marsh | 602/18 |
| 2005/0247309 | A1 | | 11/2005 | Reddick | |

* cited by examiner

*Primary Examiner*—Patricia M Bianco
*Assistant Examiner*—Keri J Nicholson
(74) *Attorney, Agent, or Firm*—Dicke, Billig & Czaja, PLLC

(57) ABSTRACT

A user or assistant operated device for elevation and forward thrusting of the jaw for mild to moderate obstructive sleep apnea is disclosed. The device includes a base configured to contact a torso of a wearer, a chin support configured to contact a jaw of the wearer, and a jack extending between the base and the chin support. In this regard, the jack is length adjustable and configured to elevate the chin support relative to the base such that the jaw is thrust forward relative to the torso.

19 Claims, 1 Drawing Sheet

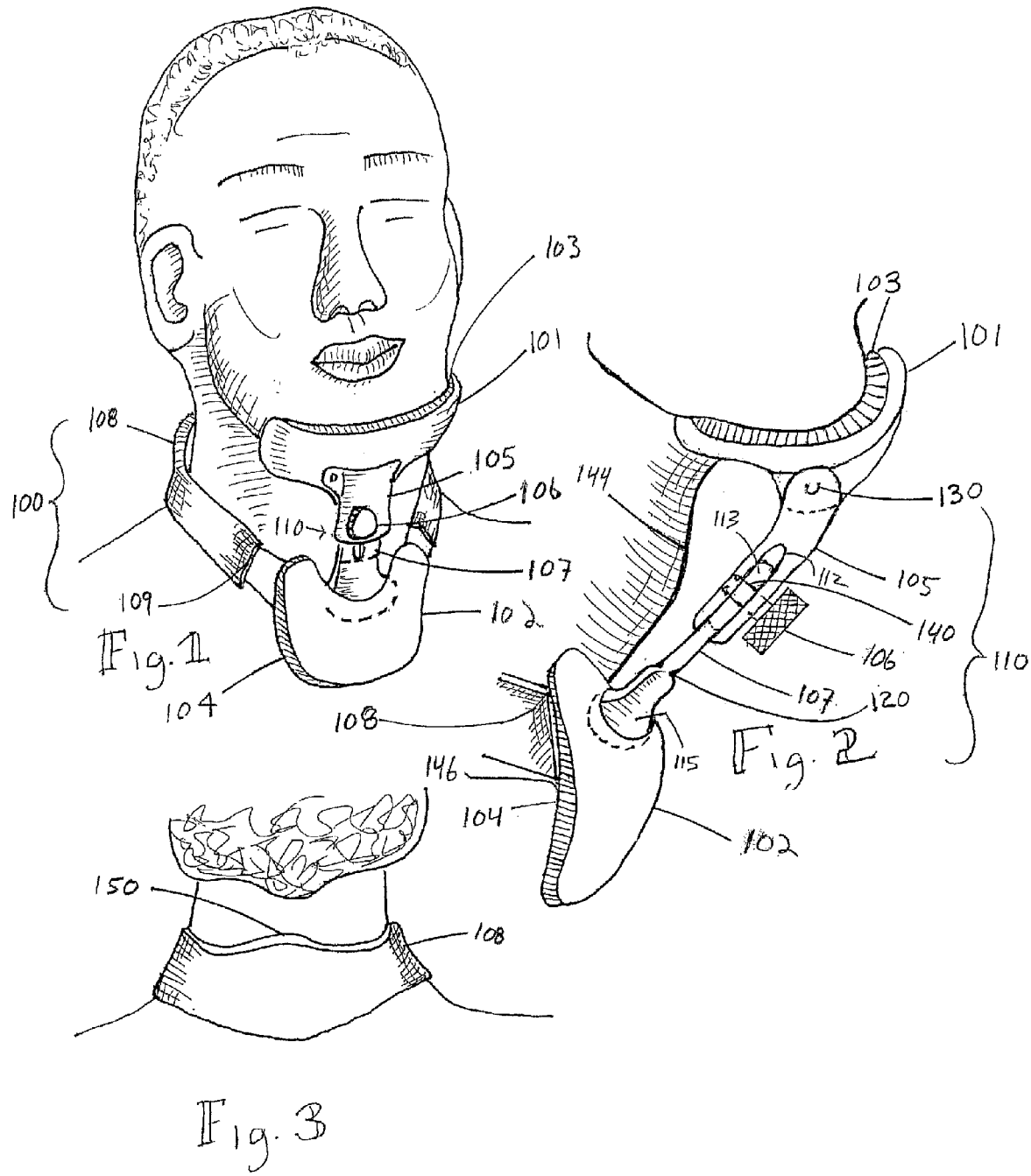

HEAD POSITIONING DEVICE FOR TREATMENT OF SLEEP APNEA

FIELD OF THE INVENTION

Aspects of the present invention relate to the treatment of sleep apnea, and more particularly, to a jaw elevating and forward thrusting device for treatment of obstructive sleep apnea of the mild to moderate type.

BACKGROUND

Sleep disorders affect up to 90% of the population, and of these various cases, sleep apnea is the most important worldwide problem, occurring in about 3 to 5% of the general population. Apnea, (Greek for no breath) is a cessation of breathing for longer than 30 seconds, however a respiratory cessation for more than 5 to 7 seconds may be uncomfortable or indicate mild clinical apnea. Respiratory periodicity does vary normally being slower during rest or sleep. In fact, short periods of apnea in which breathing ceases for a few seconds before resuming, normally occur during sleep.

The breathing rate largely determines the blood and tissue content of oxygen and carbon dioxide. When longer periods of apnea alternate with periods of 'catch up' rapid, heavy breathing, these irregular cycles are called Cheyne-Stokes respiration and may be indicative of abnormalities influencing the respiratory pacemaker located in the brain stem. Such a condition is referred to as central apnea.

Sleep apnea can be a serious even lethal problem for susceptible or debilitated cases having some intercurrent disease. Sleep apnea contributes to daytime sleepiness, inattention on the job and auto accidents. The apnea occurs in two principal forms: (1) obstructive, due to a mechanical partial blockage of respiratory passages particularly in the throat and (2) central, involving a change in the respiratory pacemaker in the brain stem. The obstructive type is far more common and has prompted a wide variety of means for treatment including weight loss regimens, throat muscular exercises, special sprays, or surgery to remove redundant tissues. Further, expensive, complex, uncomfortable, unpleasant air pressure devices have been successful in treating more complex cases of intermittent obstruction.

Anatomically, extension of the neck with forward thrusting of the jaw opens the throat passages. When applicable to the respiratory obstructive problem, jaw elevation can be remarkably helpful. A number of external appliances, neck pillows, neck bracing jaw thrusters and head traction devices have been developed for this purpose but are unwieldy, uncomfortable bulky or fixed and not freely adjustable as needed.

With the above Background in mind, improvements to, and advancement in curative devices or appliances will be welcomed by sleep apneics, and by persons having temporary obstruction due to enlargement of throat structures due to upper respiratory and/or throat infections.

SUMMARY

One aspect of the present invention provides a head positioning device for treatment of sleep apnea. The device includes a base configured to contact a torso of a wearer, a chin support configured to contact a jaw of the wearer, and a jack extending between the base and the chin support. In this regard, the jack is length adjustable and configured to elevate the chin support relative to the base such that the jaw is thrust forward relative to the torso.

Aspects of the present invention provide a simple means for elevation and forward thrusting of the jaw, serving to open the passages of the throat in a fashion similar to extending the head and neck. The device includes at least one adjustable chin cushion, at least one chest cushion and at least one simple, adjustable, extendible ratcheting 'jack' poised between the chin and chest portions that on extension lifts and forwardly thrusts the jaw.

The force to lift the jaw when in the standing position is bout 2-4 pounds, while in the supine position it is 1-2 pounds. The cushioned surface areas of embodiments of the novel jaw elevator are greater than 3 square inches, such that the direct skin capillary pressure is low and tissue erosion from excessive pressure is avoided.

The jack mechanism, in one embodiment, is user operated and can be overridden and partly or fully released by the user in case of the need for swallowing, sneezing or any uncomfortable or emergent condition requiring the removal of the device. Embodiments of the present invention provide rotation of the head about 30 to 45 degrees from a frontal position to permit a nearly full range of positions of comfort when sleeping.

The unit also includes, in one embodiment, an easily attached, applied, removed, cushioned, adjustable around the neck strap of the hook and loop type. Thus the novel device can be instantly and completely removed.

Further, in case of forced repositioning of the jaw, the elevating or jack portion is, in one embodiment, designed to slip permitting a return to the neutral jaw position. Such as may occur during a sudden and strong sneeze or gasp. In this regard, the unit is configured not only to be effective in jaw elevation and forward thrusting but also to be comfortable, easily applied and adjusted. Still further, it is easily removed and easily cleaned. Thin, soft paper handkerchiefs may be placed between the cushions and the skin, as desired or for oily or pustular skin.

Other aspects of the present invention provide for appropriate fitting and wearing during sleep with the wearer in any back or side position (facedown positions being detrimental to sleep apnea problems in that they cause the jaw to retro-displace.) During initial or trial application there is additionally included the potential for daytime training and adjusting, prior to bedtime for use in upright or reclining positions. The method further may make use of nasal decongestants when needed for additional respiratory tract opening. In regard to the above, the novel jaw elevation and forward thrusting translates into positional improvement reducing air passage restriction, efforts to breathe and considerably relieving several, primarily moderately obstructive sleep apneic problems.

Aspects of embodiments of the novel jaw elevation and forward thrusting unit include supportive components made of a suitable, tissue tolerant, cushioning compliant polymer further supporting a thermally adaptive, removable and cleanable foam cushion that prevents pressure point concentrations against the skin.

Further, in one embodiment the elevating jack is provided with a maximum torque slip joint mechanism in its elevating knob to adjust for distribution of skin contact pressure overlying facial or chest bones. This slipping or overriding of the jack also serves a safety purpose such that if the wearer so desires he can open his jaw, reducing the extended position of the jack. In one embodiment, the device is positioned on the chest and chin and adjusted to a point of a relief in respiratory effort, with optimal comfort of the chin and chest.

Other embodiments provide elevation of the cushioned parts via inflation of chin support and/or base cushions via inflatable piston(s).

In one embodiment, the jack includes a friction clutch. The user can practice overriding the jack by opening the jaw, and adjusting the friction clutch torque as desired. Embodiments of the present invention are compatible with head extension through the use of a posterior neck roll/pillow.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

FIG. 1 illustrates a perspective view of a user wearing a head positioning device according to one embodiment of the present invention.

FIG. 2 illustrates a perspective view of a head positioning device according to one embodiment of the present invention.

FIG. 3 illustrates a plan view of a back of a user's head showing a neck collar or strap of the device shown in FIG. 1.

For one skilled in the art, it will be recognized that other embodiments may be utilized and structural or logical changes may be made without departing from the scope of the present invention.

DETAILED DESCRIPTION

In the following Detailed Description, reference is made to the accompanying drawings that form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The Figures illustrate diagrammatically embodiments of the invention where a neck strap stabilizes the device and appropriately placed cushions provide footings on the chest and chin for the counterforce needed to elevate and forwardly thrust the jaw while opening the respiratory passages in the pharynx and base of the tongue.

FIG. 1 illustrates a head positioning device 100 for treatment of sleep apnea. The device 100 includes a chin support 101 configured to contact or engage a jaw of the wearer, a base 102 configured to contact or engage a torso of a wearer, and a jack 110 extending between the chin support 101 and the base 102.

With reference to FIG. 1, during use, the user's chin is comfortably placed in chin support 101 (or holder 101), and the base 102 (or chest component 102) contacts a torso of the user, thereby countering the chin and head weight to attain jaw elevation and forward thrusting. In one embodiment, the chin support 101 has a suitable cushion 103 and the base 102 includes a cushion 104. In one embodiment, the cushions 103, 104 are thermally adaptive and configured to conform to anatomy of the wearer. For example, in one embodiment, the cushions 103, 104 are inflatable cushions including a piston and an air bladder. Alternatively, the cushions 103, 104 can assume a variety of other forms, and in some embodiments, are eliminated.

In one embodiment, the jack 110 includes or defines an upper portion 105 coupled to the chin support 101, a lower portion 107 coupled to the base 102, and a knob 106 connected to one of the portions 105, 107 and configured to selectively secure the portions 105, 107 together.

In one embodiment, the tightening knob 106 includes a means for immediately retracting the lack to decline the jaw comprising a slip joint mechanism configured to permit the lower portion 107 of the jack 110 to releasably slide into the upper portion 105 when a threshold force is applied to the chin support 101.

In one embodiment, a cushioned neck strap 108 or collar 108 encircles the user's neck and is adjustable using hook and loop fastener means 109. In one embodiment, the adjustable, cushioned neck strap 108 attaches to and extends from opposing sides of the base 102.

As described below, the device 100 is adapted to suitably accommodate a variety of user chin elevations, as well as chin and chest contours via the jack 110 and corresponding assembly of the jack 110 relative to the chin support 101 and the base 102. With additional reference to FIG. 2 (otherwise illustrating a lateral view of the device 100), in one embodiment, the slidable relationship of the upper and lower portions 105, 107 is achieved by the upper portion 105 of the jack 110 defining a receptacle 112, and the lower portion 107 defining a shaft 113 that is slideably received within the receptacle 112. Alternatively, the upper portion 105 can be configured to be slidably received within a corresponding aperture formed by the lower portion 107. Regardless, the upper portion 105 is slidably connected with the lower portion 107 such that an overall height or length of the jack 110 (and thus of the device 100) can easily be altered as desired by the user. Relative to the one embodiment of FIGS. 1 and 2, the upper and lower portions 105, 107 are selectively locked to one another via the knob 106. For example, the knob 106 can include a threaded shaft 140 passing through a hole in a front of the upper portion 105 and a slot (best shown in FIG. 1) in the lower portion 107, and threadably engaged in a hole in a back of the upper portion 105. In one embodiment, the upper movable portion 105 of the jack 110 is clamped using the adjustable knob 106 with a pincer effect against the lower portion 107 of the jack 110. In one embodiment, the threaded rod 140 passing through the slotted upper portion of the jack 110 creates the sliding but overcoming friction that maintains the chin position.

In one embodiment, the lower portion 107 and the base 102 combine to define a ball and socket joint 115, such that the lower portion 107 is configured for pivoting movement relative to the base 102. Further, in one embodiment, the lower portion 110 includes a bendable portion 120 (e.g., malleable metal) that allows the user to bend the lower portion to a desired shape.

In one embodiment, the upper portion 105 is connected to the chin support 101 by a hinge 130. In this manner, the jack 110 is hinged to the chin support 101 such that the chin support 101 can move or pivot laterally relative to the upper portion 105.

The ball and socket 115 of the lower portion 107 of the jack 110 permits lateral excursions of the user's head to about 30-45 degrees to either side of a direct forward position. The bendable portion 120 of the lower jack and the hinge 130 at the articulation between the upper jack and the chin support 101 permit motions and adjustments for the particular user to assure adequate forward clearance of the jack 110 from the anterior contour 144 of the neck. In one embodiment, the base 102 defines at least one relief contour 146 configured to provide a relief space for receiving skin anterior to a neck of the wear.

FIG. 3 illustrates a posterior view of the user's neck showing the cushioned contour 150 of the adjustable collar or strap 108.

While a preferred embodiment of the novel jaw elevating and forward thrusting device 100 has been illustrated, someone skilled in the mechanical arts may arrive at variations of the design without departing from the scope of the present invention. For example, the jack 110 can serve as a frictionless clutch (or a separate clutch mechanism included) that allows a user to easily override a jaw position in the event of, for example, sneezing or occurrence of a choking sensation.

Method and Example of Use

With reference to the FIGS. 1-3, the device 100 is first applied as a practice trial during upright and reclining positions of the neck and head. The device 100 is adjusted for comfortable fit using the controlled adjustment means for jack 110 elevation. The comfortable collar or strap 108 is placed around the neck and adjusted using the hook and loop tabs 109, for example. The jaw and chest cushions 103, 104, respectively, are then further adjusted for optimal position and comfort. The jack elevation is further adjusted as the user breathes, determines the best combination of jaw elevation and forward thrusting then tightens the jack elevation knob 106 to retain that preferred position. If a suitable forward neck clearance is not readily attained, the device 100 is removed and a slight bend is placed in the lower jaw portion (i.e., the bendable portion 120). The device 100 is then reapplied and the user laterally rotates his head to determine the range of motion permitted by the modified ball and socket junction 115 at the lower end 107 of the jack 110 and base/chest 102 component.

The user then practices the overriding of the jack 110 mechanism while forcing an imitated sneeze, swallowing and wide opening of the jaw. This exercise assures the user as to the safety and continual control he has over jaw elevation and forward thrusting under sudden circumstances where unforeseen excessive jaw opening might be required. The device 100 is also easily removed and replaced for facial or dental hygiene or for the need to find a new position of comfort such as against various pillows or in the absence of a pillow.

On arising after the period of sleep, the device 100 is removed and simply wiped clean or washed as needed. The device 100 may be stored in a convenient drawer or container at bedside. All components in contact with the user's skin are soft, hypoallergenic and tissue tolerant. Manually operated parts have no sharp edges or protrusions that might cause injury to the user or other attending person. The device 100 can be applied and adjusted by other parties when applied to weakened or paralyzed users.

Advantages

The invention has the novel ability to elevate and forwardly thrust the jaw of a person having mild to moderate respiratory obstruction of throat and tongue base origin using a simple, user adjusted, cushioned jack mechanism. The method is extremely user friendly and obvious in function, under control by the user at all times. The device and method can be used with or without adjunctive neck support and/or medication that augment respiratory function as required by the particular user. The user employing the novel device simply applying it and adjusting it while upright or reclining, begins using practice applications with adjustment for an optimal effect on his respiration. Further, the mechanisms permit continuous adjustment of jaw position and thrust as desired. Sudden demands by the user, such as for sneezing or the sensation of strangulation, readily cause the extent of elevation of the jaw to be eased and the device may be removed.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

While the preferred embodiments of the invention have been described, it should be understood that various changes, adaptations and modifications may be made therein by those skilled in the art without departing from the spirit of the invention and the scope of the appended claims.

The application of the jaw elevator and forward thruster device is devoid of any undesirable side effect such as entrapment of the user's neck or jaw. It has an easy override of the position that has been firmly but reversibly adjusted to the user's optimal use. Both the adjustment and release effects are immediate and continuous. With the device disclosed herein, the user or an assistant using logical, tactile hand maneuvers advantageously adjusts the mechanism to hold the jaw position yielding an optimal effect on respiration. The device is constructed of tissue tolerable polymers and the elevating adjustment can be attached to the chest and chin cushion components in a variety of ways. Preferred means to deliver the desired jaw elevation and forward thrusting are disclosed here although persons skilled in the mechanical arts can adapt the concept to a variety of means to cause desirable jaw elevation force and ratcheting mechanism without departing from the spirit of the invention. No other fully adjustable and emergent released jaw elevating and forward thrusting device or method serving this application or in combination with an overall neck support under user control is known to exist at this time.

What is claimed is:

1. A head positioning device for treatment of sleep apnea comprising:
   a jack comprising:
      an upper portion;
      a lower portion that is slidable relative to the upper portion; and
      a tightening knob to selectively lock the upper portion relative to the lower portion;
   a base configured to contact a torso of a wearer, wherein the lower portion is coupled to the base by a ball and socket joint; and
   a chin support configured to contact a jaw of the wearer, wherein the upper portion is hinged to the chin support;
   wherein the jack is length adjustable and wherein the distance between the base and the chin support is fixed when the tightening knob is in a locked position to elevate the chin support relative to the base such that during use, a user's jaw is thrust forward relative to the user's chest.

2. The head positioning device of claim 1, further comprising:
   a strap coupled to opposing sides of the base, the strap configured to extend around a neck of the user.

3. The head positioning device of claim 2, wherein the strap is an adjustable strap.

4. The head positioning device of claim 1, wherein at least one of the base and the chin support includes a cushion.

5. The head positioning device of claim 4, wherein the cushion is thermally adaptive and configured to conform to anatomy of the wearer.

6. The head positioning device of claim 1, wherein the lower portion defines a shaft that is slideably received by a receptacle of the upper portion.

7. The head positioning device of claim 1, wherein the lower portion includes a bendable portion.

8. The head positioning device of claim 1, wherein the tightening knob operates as a slip joint mechanism configured to permit the lower portion of the jack to releasably slide into a receptacle of the upper portion when a threshold force is applied to the chin support.

9. The head positioning device of claim 8, wherein the tightening knob operates as a friction clutch.

10. The head positioning device of claim 1, wherein the base defines at least one relief contour configured to provide a relief space for receiving skin anterior to a neck of the wear.

11. A method of relieving sleep apnea comprising:
    providing a wearer patient with a head positioning device, the head positioning device comprising:
        a jack having an upper portion, a lower portion and a tightening knob;
        a chin support configured to contact a jaw of the wearer, wherein the chin support and the upper portion of the jack are operably connected with a hinged coupling; and
        a base configured to contact a chest of the wearer, wherein the base and the lower portion of the jack are operably connected with a ball and socket joint;
    securing the base with respect to the chest;
    positioning the jaw of the wearer into the chin support;
    adjusting the jack to elevate the jaw relative to the chest to open respiratory throat passages; and
    maintaining the chin support and the base at a fixed distance apart from each other with the tightening knob that engages the upper portion and the lower portion to maintain the respiratory throat passages in the open configuration while permitting a head of the wearer patient to rotate with respect to the chest.

12. The method of claim 11, wherein adjusting the jack includes extending the jack by ratcheting the upper portion of the jack relative to the lower portion of the jack.

13. The method of claim 11, wherein adjusting the jack includes turning the tightening knob coupled to a receptacle of the upper portion of the jack in positioning a shaft extending from the lower portion of the jack into the receptacle.

14. The method of claim 11, wherein the head positioning device includes means for immediately retracting the jack to declinate the jaw relative to the chest.

15. The method of claim 14, wherein the tightening knob selectively locks the upper portion relative to the lower portion.

16. The method of claim 14, wherein the retracting means releases when a threshold force is applied to the chin support.

17. A head positioning device for treatment of sleep apnea comprising:
    a base configured to contact a torso of a wearer;
    a chin support configured to contact a jaw of the wearer; and
    a single jack operably connecting the base and the chin support, wherein the single jack comprises:
        an upper portion that is hinged to the chin support;
        a lower portion that is slidable relative to the upper portion, wherein the lower portion is coupled to the base by a ball and socket joint; and
        a tightening knob to selectively lock the upper portion relative to the lower portion, wherein the jack is length adjustable and wherein the distance between the base and the chin support is fixed when the tightening knob is in a locked position to elevate the chin support relative to the base such that during use, a user's jaw is thrust forward relative to the user's chest.

18. The head positioning device of claim 17, wherein the lower portion defines a shaft that is slideably received by a receptacle of the upper portion.

19. The head positioning device of claim 17, wherein the tightening knob operates as a slip joint mechanism configured to permit the lower portion of the jack to releasably slide into a receptacle of the upper portion when a threshold force is applied to the chin support.

* * * * *